United States Patent
Gerade et al.

(10) Patent No.: US 8,643,668 B2
(45) Date of Patent: Feb. 4, 2014

(54) MEDICAL IMAGING VIEWER

(75) Inventors: Graham D. Gerade, Brighton, MA (US); Hamid Tabatabaie, Waban, MA (US); Amy J. Vreeland, Waban, MA (US)

(73) Assignee: Lifeimage, Newton, MA (US)

( * ) Notice: Subject to any disclaimer, the term of this patent is extended or adjusted under 35 U.S.C. 154(b) by 579 days.

(21) Appl. No.: 12/627,391

(22) Filed: Nov. 30, 2009

(65) Prior Publication Data

US 2010/0141673 A1 Jun. 10, 2010

Related U.S. Application Data

(60) Provisional application No. 61/118,732, filed on Dec. 1, 2008.

(51) Int. Cl.
*G09G 5/00* (2006.01)
*G06K 9/40* (2006.01)

(52) U.S. Cl.
USPC ............................ 345/619; 345/625; 382/254

(58) Field of Classification Search
USPC .................................. 345/600–625; 382/254
See application file for complete search history.

(56) References Cited

U.S. PATENT DOCUMENTS

| 5,416,602 | A | 5/1995 | Inga et al. |
| 5,727,084 | A | 3/1998 | Pan et al. |
| 5,774,133 | A | 6/1998 | Neave et al. |
| 6,252,608 | B1 | 6/2001 | Snyder et al. |
| 6,424,730 | B1 | 7/2002 | Wang et al. |
| 6,556,724 | B1 | 4/2003 | Chang et al. |
| 6,574,629 | B1 | 6/2003 | Cooke, Jr. et al. |
| 7,167,181 | B2 | 1/2007 | Duluk, Jr. et al. |
| 7,362,915 | B2 | 4/2008 | Vuylsteke |
| 2002/0016718 | A1 | 2/2002 | Rothschild et al. |
| 2002/0091659 | A1 | 7/2002 | Beaulieu et al. |
| 2002/0114530 | A1 | 8/2002 | Duarte |
| 2002/0196848 | A1* | 12/2002 | Roman ................. 375/240.08 |
| 2006/0092169 | A1* | 5/2006 | Wetzel ..................... 345/582 |
| 2007/0145282 | A1 | 6/2007 | Campbell |
| 2007/0177779 | A1 | 8/2007 | Dennison |
| 2007/0211929 | A1 | 9/2007 | Beddoe |
| 2008/0081991 | A1 | 4/2008 | West et al. |
| 2008/0120372 | A1* | 5/2008 | Kariathungal et al. ...... 709/204 |
| 2008/0140722 | A1 | 6/2008 | Jakobovits |
| 2009/0263037 | A1* | 10/2009 | Qiu et al. .................... 382/254 |

OTHER PUBLICATIONS

Gillespy et al., Displaying Radiologic Images on Personal Computers, Aug. 1993, Journal of Digital Imaging, vol. 6, No. 3, pp. 151-163.*
Treml, A Web Based Medical Image Viewer, Apr. 2008, Department of Computer Science and the Faculty of the University of Wisconsin-La Crosse, pp. iii-51.*
International Search Report mailed Jan. 28, 2010 in corresponding International Application No. PCT/US2009/066131.
European Search Report dated Dec. 18, 2012 in corresponding European Application Serial No. 09830931.3.

* cited by examiner

*Primary Examiner* — Xiao M. Wu
*Assistant Examiner* — Matthew D Salvucci
(74) *Attorney, Agent, or Firm* — Chapin IP Law, LLC

(57) ABSTRACT

A medical imaging viewer application processes and interactively displays grayscale images having a higher grayscale range (bit depth) on a platform optimized for a lower grayscale range. The application additionally provides pixel calculations based on the user's selection of a window center and a window width.

21 Claims, 14 Drawing Sheets

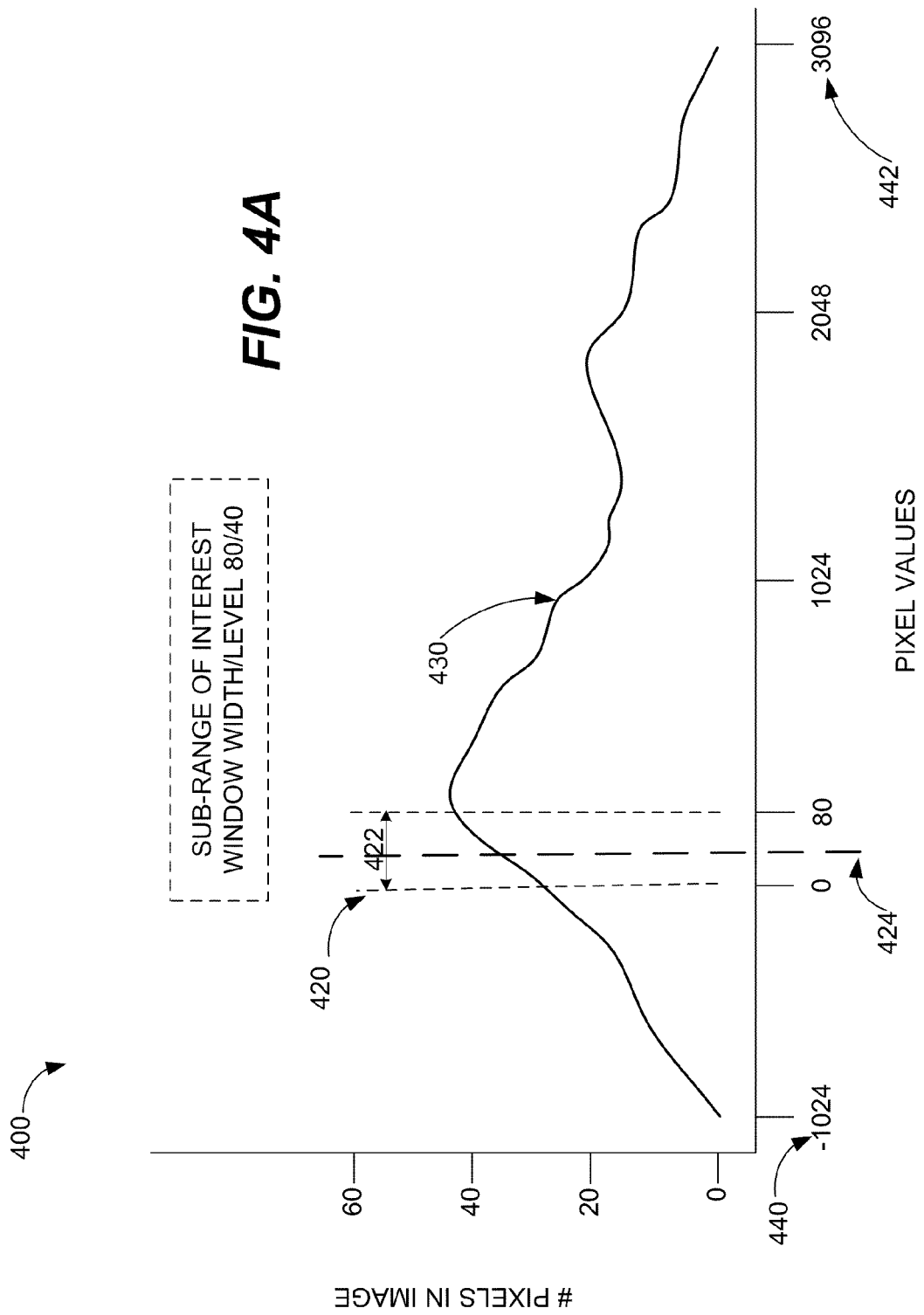

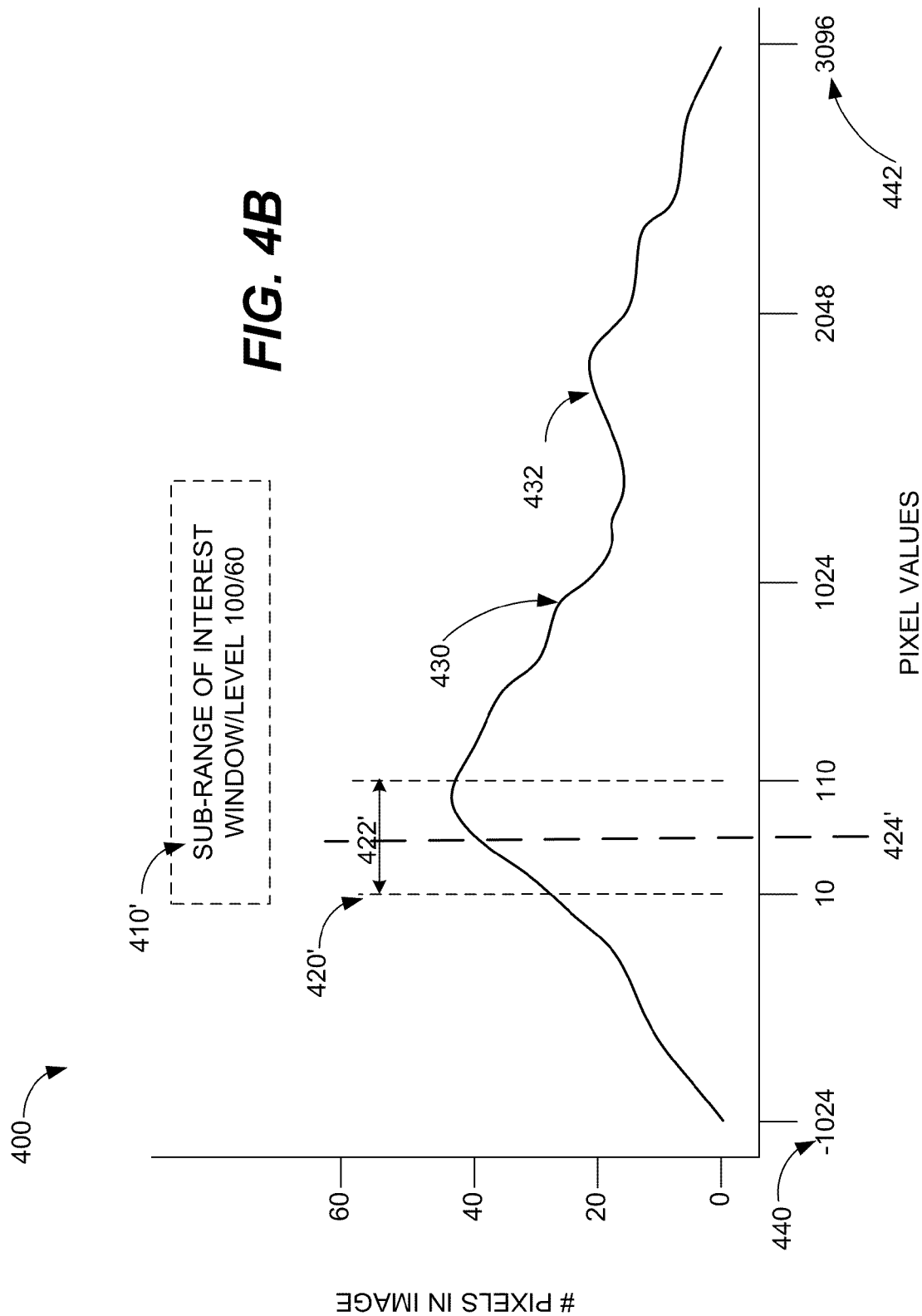

# MEDICAL IMAGING VIEWER

PRIORITY TO EARLIER FILED PROVISIONAL PATENT APPLICATIONS

This application claims the benefit of the filing date of: earlier filed U.S. Provisional Patent Application having Ser. No. 61/118,732 entitled "MEDICAL IMAGING VIEWER," filed Dec. 1, 2008 that shares co-inventorship with the present application. The entire teachings and contents of this Provisional Patent Application are hereby incorporated by reference herein in their entirety.

BACKGROUND

Physicians around the world access medical images to help diagnose and treat patients and disease, to collaborate with colleagues and to provide decision support and education. Physicians display medical images at various locations including hospitals, doctor's offices, and on various devices including but not limited to high resolution special purpose displays, PCs, cell phones, PDAs, etc.

Clinical quality images can be 12 bits of depth or more, and can be displayed with 4096 or more shades of gray. This broad grayscale range permits miniscule pathological or structural abnormalities (such as tumors, calcifications, and fractures) to be viewable to the human eye for diagnostic purposes. Providing sufficient grayscale reproduction on web-based platforms presents challenges. Many existing solutions require an operating platform (e.g. Windows, Mac, and Linux) specific implementation (e.g. ActiveX controls, Netscape plug-ins). "Pure" web browser based solutions require that the Web server generate and deliver images for every presentable situation. This approach is very server and network intensive and therefore it is very difficult to achieve interactive manipulations with this approach. It is even more difficult to scale these approaches to an internet based solution. Rendering is sometime facilitated by the use of rendering engines which convert specifications for images into pixels for display on computer screen (e.g. Adobe Flash, Microsoft Silverlight). The rendering engines can include specialized software or hardware components.

SUMMARY OF THE INVENTION

Conventional techniques which typically rely on special purpose hardware and software that enable interactive manipulation of medical images, for example DICOM images, are not operable in certain limited bandwidth and computation environments, such as web browsers operating on personal computer, cell phones and other mobile devices. Current approaches in these limited environments do not allow for interactive manipulation and display of the full bit depth of images. These conventional approaches do not provide acceptable performance or usability by practitioners in the field. Still other approaches used in these limited environments rely on servers that pre-process the data and continuously send updated images to clients. These approaches are generally a compute and bandwidth intensive method, and there are limitations with scalability, bandwidth and efficiency when it comes to serving large numbers of simultaneous users. Other approaches require special purpose software applications.

For example, one type of conventional viewer relies on software that requires a proprietary downloadable "client" to the user's computer. When used inside a hospital, this approach requires the endorsement of hospital IT departments who will have to support the downloadable client. Furthermore, continuous tone, clinical quality images can have 12 to 16 or more bits of depth, and some clinical review applications require the ability to visualize subsets of that range at full fidelity. Some commercial rendering engines, for example the Adobe® Flash® player, are designed and optimized to handle true-color images which are only capable of operating on and rendering 8-bits of continuous tone pixel data. Medical imaging viewers based only on these engines may be limited to too few shades of gray for diagnostic purposes. Furthermore, these viewers will not perform interactive manipulations sufficiently fast enough for clinical use.

Techniques discussed herein deviate with respect to conventional applications such as those discussed above as well as additional techniques also known in the prior art. In particular, embodiments herein enable a user to view relatively high bit depth images and interact with the display of these images for diagnostic review operable in such limited environments as those described above. Examples of these environments are available on standard personal computers and mobile devices with commercially available rendering engines.

For example, a technique as further described herein involves acquiring a first image having a first bit depth, generating sub-range image sets, where each set includes sub-range images at a second bit depth and selecting a sub-range image for display. The technique further includes performing pixel calculations on the selected sub-range image in a rendering engine operable to perform pixel calculation on the selected sub-range image at the second bit depth and displaying the image using the rendering engine. Such a technique provides accelerated calculations which allow interactive display of certain per-pixel calculations on images having a depth of more than 8 bits per pixel.

Another technique includes enabling interactive visualization of certain medically relevant calculations on continuous-tone digital images. More specifically, the method leverages generally available, rendering engines capable of performing optimized 8-bit Red Green Blue (RGB) per-pixel digital imaging calculations.

When performing calculations on a source image that has no more than 8-bits per pixel, interactive calculations are achieved with available optimized 8-bit RGB operations. When the source image has more than 8-bits per pixel, simple mechanisms that map to 8-bits will not correctly handle calculations (and therefore visualization) on sub-ranges of the image. One example of this problem occurs in medical imaging; when visualizing a "Value of Interest" linear transformation on the pixel data (generally referred to as Windowing and Leveling).

One example is the visualization of a typical CT image of the head which may include 12-bits per pixel (an image depth of 12-bits). If users are interested in visualizing slight variations in tissue density as is found in the human brain, then a linear transform of the image is required to focus in on a narrow range of pixel values from the source image. Using a direct linear mapping from the full 12 bit range to an 8 bit image will result in significant loss of grayscale values that would otherwise be available in the original source image. Brute force calculations are possible, but due to the number of calculations for typical images this approach does not produce an interactive visualization experience that is acceptable for medical imaging and display.

Yet other embodiments herein include software programs to perform the steps and operations summarized above and disclosed in detail below. One such embodiment comprises a computer program product that has a computer-readable medium including computer program logic encoded thereon that, when performed in a computerized device having a coupling of a memory and a processor and a display, programs the processor to perform the operations disclosed herein. Such arrangements are typically provided as software, code and/or other data (e.g., data structures) arranged or encoded on a computer readable medium such as an optical medium (e.g., CD-ROM), floppy or hard disk or other a medium such as firmware or microcode in one or more ROM or RAM or PROM chips or as an Application Specific Integrated Circuit (ASIC). The software or firmware or other such configurations can be installed onto a computerized device to cause the computerized device to perform the techniques explained herein.

BRIEF DESCRIPTION OF THE DRAWINGS

The foregoing and other objects, features, and advantages of the invention will be apparent from the following more particular description of preferred embodiments herein, as illustrated in the accompanying drawings in which like reference characters refer to the same parts throughout the different views. The drawings are not necessarily to scale, with emphasis instead being placed upon illustrating the embodiments, principles and concepts. For clarity, some of the images in the drawings have been inverted in grayscale (e.g., black to white and white to black).

FIG. 4A is a diagram of a histogram of an original image at a relatively higher image bit depth than a rendering image with a first selection of a SROI according to an embodiment herein;

FIG. 4B is a diagram of a histogram of the original image of FIG. 4A using a second selection of a SROI according to an embodiment herein;

DETAILED DESCRIPTION

When visualizing a source image that has more than 8-bits per pixel, embodiments according to this invention allow for leveraging readily available optimized 8-bit image calculations to provide interactive display of these calculations on partial ranges of the full bit depth. Embodiments disclosed herein, dynamically generate 8-bit Red Green Blue (RGB) or Red Green Blue Alpha (RGBA) "sub-range" images that are used for display and calculations of sub-ranges of an image with more than 8 bits per pixel grayscale. Operations on these sub-range images benefit from the optimized imaging operations in certain rendering engines. The sub-range images are then swapped in during interactive display of the image calculations, resulting in effective display of the full range at the optimized rates of calculation.

Figure 1:
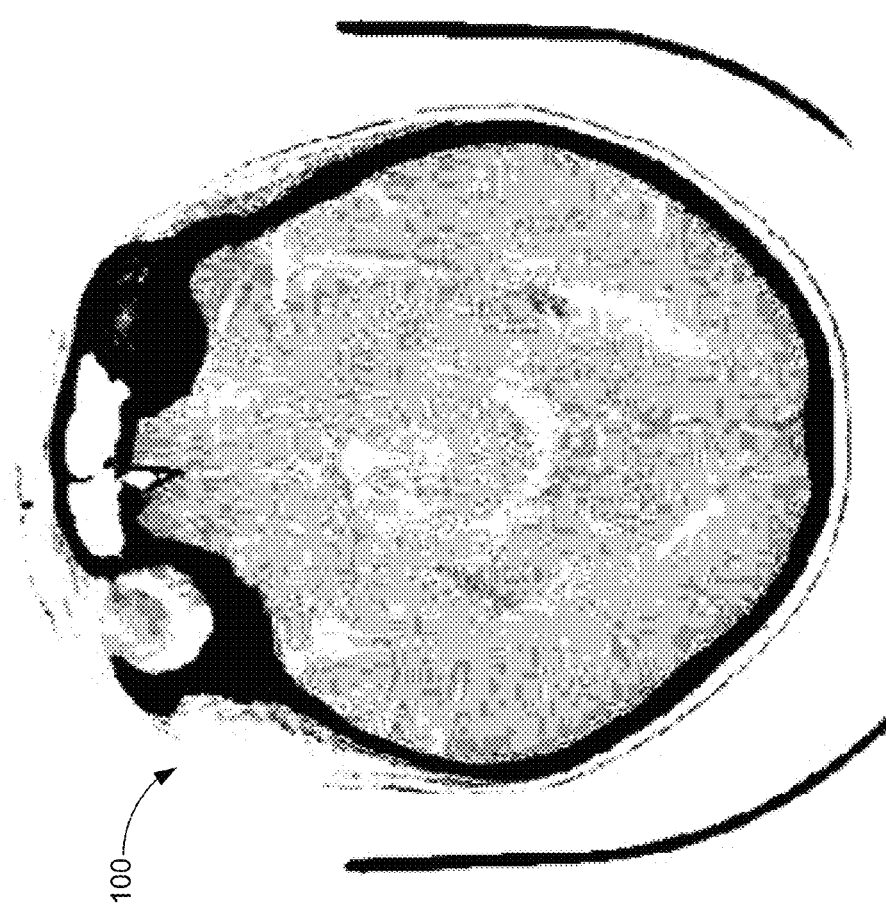
FIG. 1 is a diagram illustrating a prior art 8-bit display of medical image selection of window center and window width and the resulting image displayed.

FIG. 1 is a diagram of a higher bit-depth image (e.g., 12 to 16 bits) displayed as image 100 at a relatively lower image bit depth, here 8 bits per pixel. Image 100 is an example of an attempt using prior art methods to render a sub-range calculation on an 8-bit image that is a linear mapping of the full range of the original 12-bit source image. Here, certain features in the original image are obscured by pixelation effects in the image due to the lower image bit depth.

Figure 2:
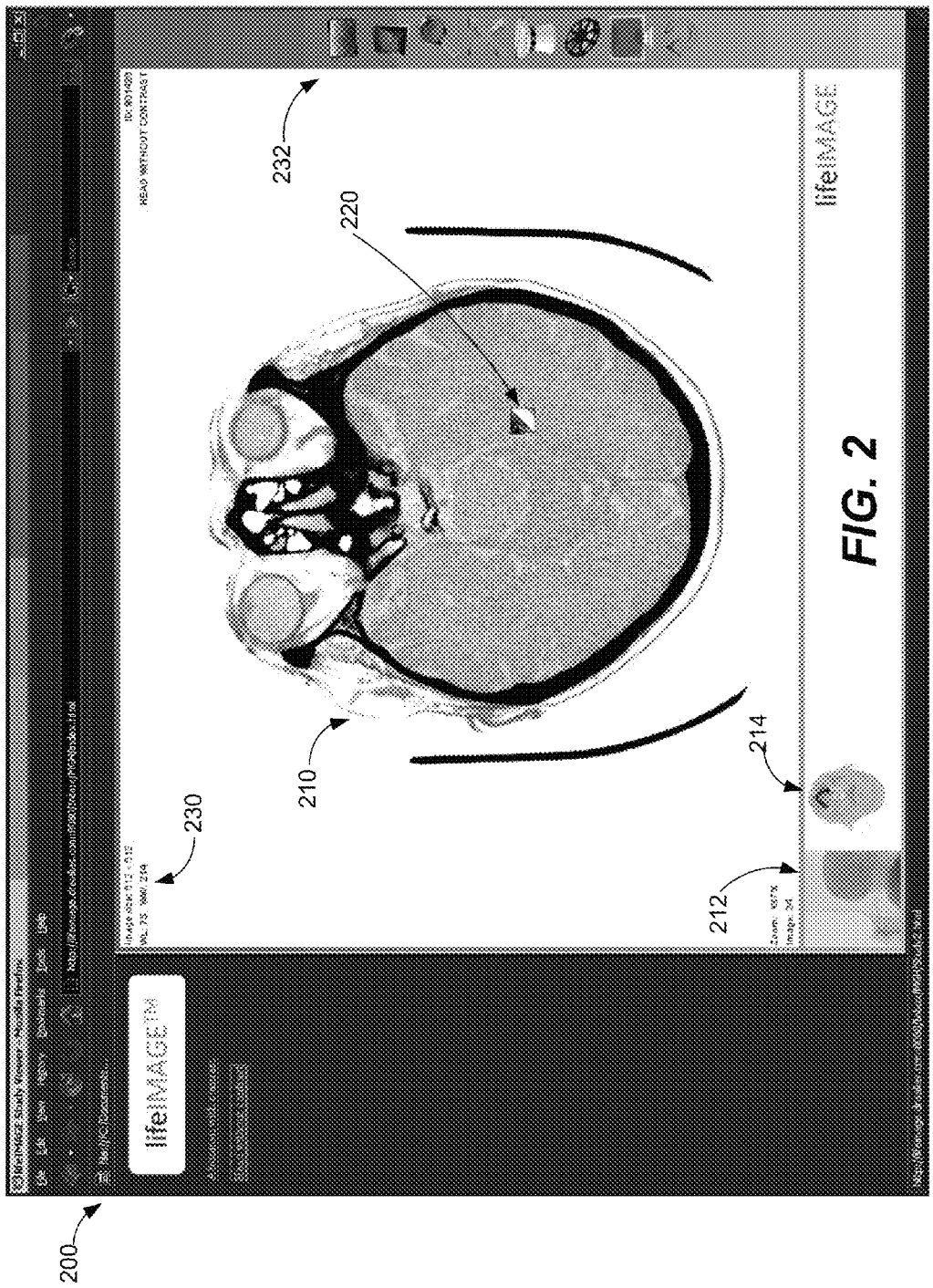
FIG. 2 is a diagram illustrating a user interface including tools for a selection of window center (WC) and window width (WW) and a resulting image displayed according to an embodiment herein.

FIG. 2 is a diagram illustrating an exemplary user interface 200 displaying an exemplary image 210 showing improved detail compared to the prior art image of FIG. 1, resulting from using sub-range image calculations according to one embodiment of the invention. The interface includes a tool 220 for a selection of window level (WL) (also referred to as window center (WC)) and window width (WW), thumbnail displays of related images 212 and 214, a display 230 of image parameters and user selections and icons 232 representing additional image processing tools. In one embodiment, the selection of the window center and a window width is identified based on monitoring movement of a pointer device having an indicator in a viewing region of a display screen, here tool 220.

A range can be defined as all possible values for a given pixel value according to an image bit depth. For example, an 8-bit per pixel image can have values 0 to 255 for each pixel and has a range of 256. A 12-bit per pixel image can have values 0 to 4095 for each pixel and has a range of 4096. A sub-range image is an image including only those pixel values specified by the beginning and end values of the sub-range. By using tool 220 or other selection tools, a user effectively selects a sub-range of interest (SROI), and the SROI is used to select a sub-range image to use for image calculations and display.

The inventors have discovered the ability to operate on these sub-range images using available 8-bit RGB or RGBA runtime optimized calculations of conventional rendering engines. The interactive visualization of the dataset operates on these sub-range images. Sub-range images are generated from the original full-depth source image and represent a particular continuous range of pixel values. The sub-ranges images are chosen such that there is an overlap of original pixel values. This pixel value overlap is a component that allows the seamless transition between sub-range images during interactive visualizations. When the calculations require pixel values that are outside the current sub-range image, an adjacent sub-range image is swapped in for display.

Figure 3A:
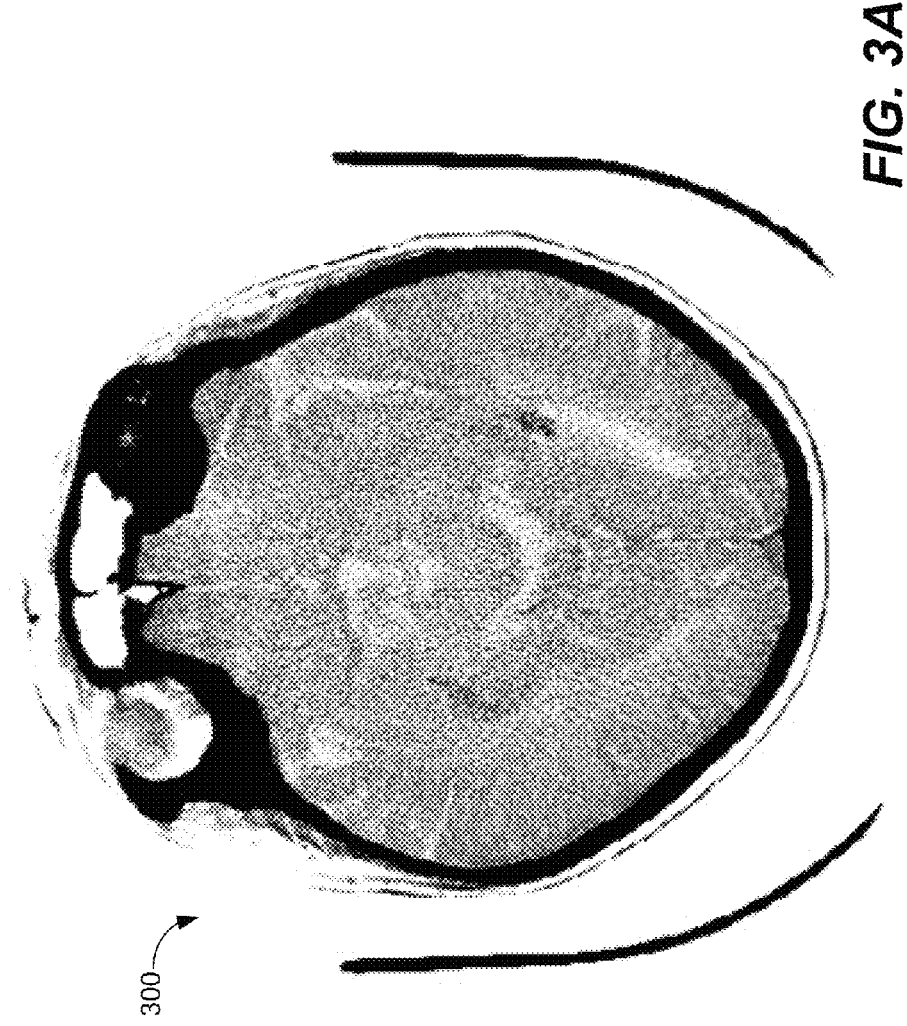
FIG. 3A is a diagram of a screen displaying a sub-range image with a first selection of window center and window width according to an embodiment herein.

FIG. 3A is a diagram of a screen of user interface 200 displaying a sub-range image 300 with a first selection of window center and window width. The original image depth, 12 bits per pixel, is at a relatively higher bit depth than the rendering engine use to process the image. The sub-range image 300 being shown is a pre-calculated sub-range image with appropriate linear calculations applied to achieve the proper visualization of the specified width and center values according to a user selected SROI. The window width (WW)

and the window center (WC) are optionally shown on the display screen. Here the user has made a further selection of WW/WL of 80/40, window width and window level (window center).

Figure 3B:
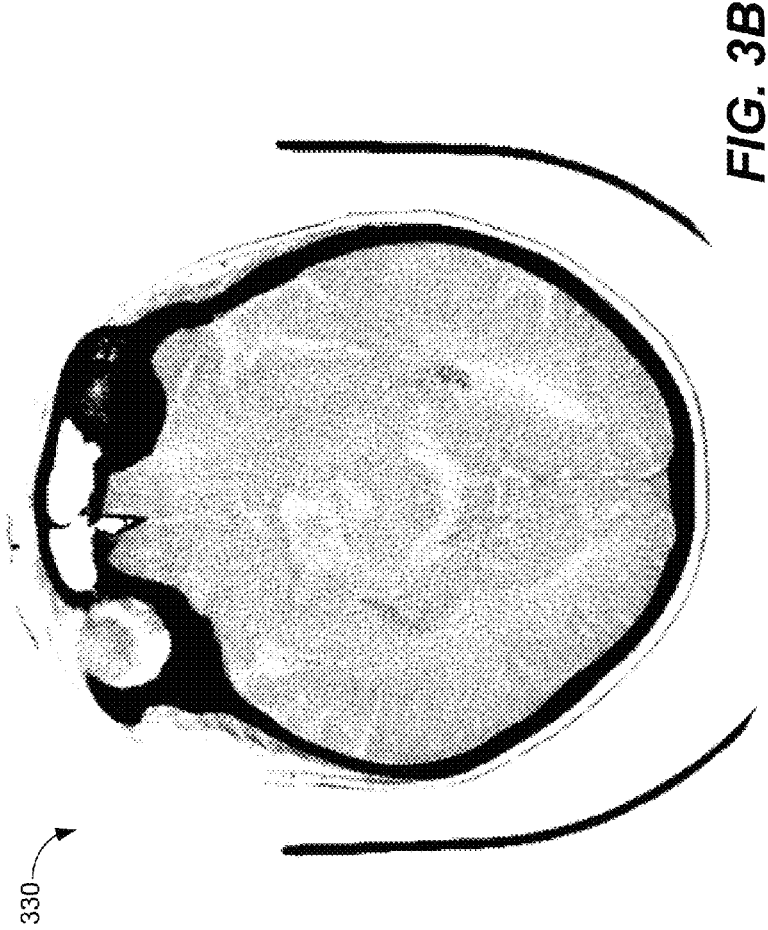
FIG. 3B is a diagram of a screen displaying the sub-range image of FIG. 3A with a second selection of window center and window width.

FIG. 3B is a diagram of a screen displaying the sub-range image 300 of FIG. 3A with a second selection of window center and window width. Here the user has made a further selection of WW/WL of 100/60, window width and window center and the resulting image 330 shows additional features.

FIG. 4A is a diagram of a histogram 400 of an original image at a relatively higher image bit depth than a rendering image used to render an image. Curve 430 represents the number of pixels for each pixel value across the range of an original image, here a 12-bit depth image resulting in a range of 4096 pixel values. The pixel value range is scaled from minus 1024 to 3096. Negative pixel values are used in some embodiments so that, for example, the standard CT Hounsfield window/level values can be depicted. A SROI 420 having width 422, here 80 and a window level or center 424, here 40, is used to select a corresponding sub range image with a first selection of a SROI according to an embodiment herein. Although with the window with less than 256 all of the grayscale cannot be used, the goal is to ensure that the original values are all represented.

FIG. 4B is a diagram of a histogram 400 of the original image of FIG. 4A using a second selection of an SROI 420'. SROI 420' indicators window width 422', here 100 and window level or center 424, here 60 depict the range as a subset of the available pixel values in the original source image.

Figure 5:
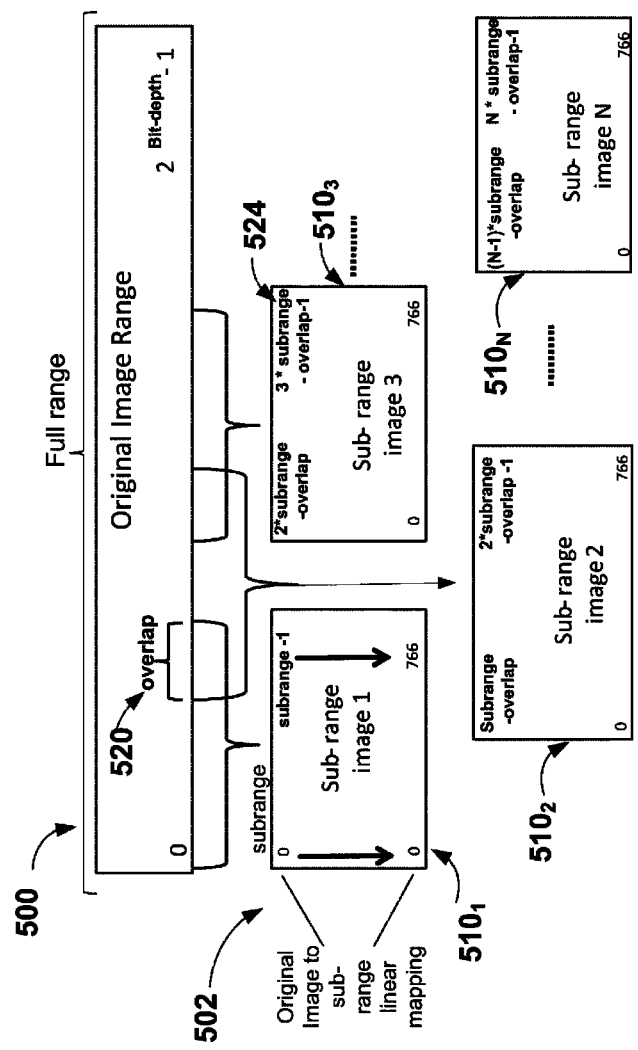
FIG. 5 is a diagram of generated sub-range images representing a subset of the available pixel values in an original source image according to an embodiment herein.

Referring to FIG. 5, a sub-range image set 502 includes plurality of generated sub-range images $510_1$-$510_N$ (generally referred to as sub-range image 510) representing a subset of the available pixel values in an original source image 500 at a first bit depth. A sub-range of interest (SROI) and predetermined overlap 520 parameters are used to determine the range and values of the sub-range images 510. These sub-range images $510_1$-$510_N$ map the original pixel values in the original source image 500 to the available grayscales in the 8-bit sub-range image. In one embodiment, the rendering engine operates at a lower second bit depth than the first bit depth of the original source image 500. In certain embodiments, a rendering engine provides a plurality of channels, each operating at a second bit depth which expands the gray scale using the plurality of channels to provide multichannel gray levels. In one embodiment, the multichannel gray scale is filtered to provide true gray scale for display.

Other embodiments use 8-bits as the second bit depth and the plurality of channels are either RGB or RGBA. In one embodiment where packed RGB values are used, there are 766 unique grayscales. The number of grayscales is derived from the number of channels, three, times the number of grays in 8-bit (253) minus the two end points (256*3-2=766). The range indicators 524 on top of the sub-range images define the source image pixel values that are represented for that sub-range image. The sub-range images can be pre-calculated or dynamically calculated by looping through the original image and creating the sub-range image. The first image at the first bit depth is mapped into sub-ranges at a second bit depth after a sub-range is selected.

In one embodiment, the sub-range values and overlaps are predetermined. These values can be a function of the application, the image type, for example a computed radiography (CR) as compared to a computed tomography (CT) image. These values can be determined by user preference and in alternate embodiments can be set dynamically based on such factors, for example, the desired minimum produced shades of gray, quality of display hardware. For example, a user might set the overlaps and sub-range values to minimally achieve rendering 200 Just Noticeable Differences (JNDs) on a device.

Other configurations of sub-ranges, number of sets, number of sub-range images and overlaps can be based on the dynamic range and characteristics of the first image. For example, the image can be a DICOM medical image with computed tomography (CT), Computed Radiography (CR), Magnetic Resonance (MR), Digital Radiography (DX), Mammography (MG) or Intra-oral Radiography (IO) specific modality.

Figure 6:
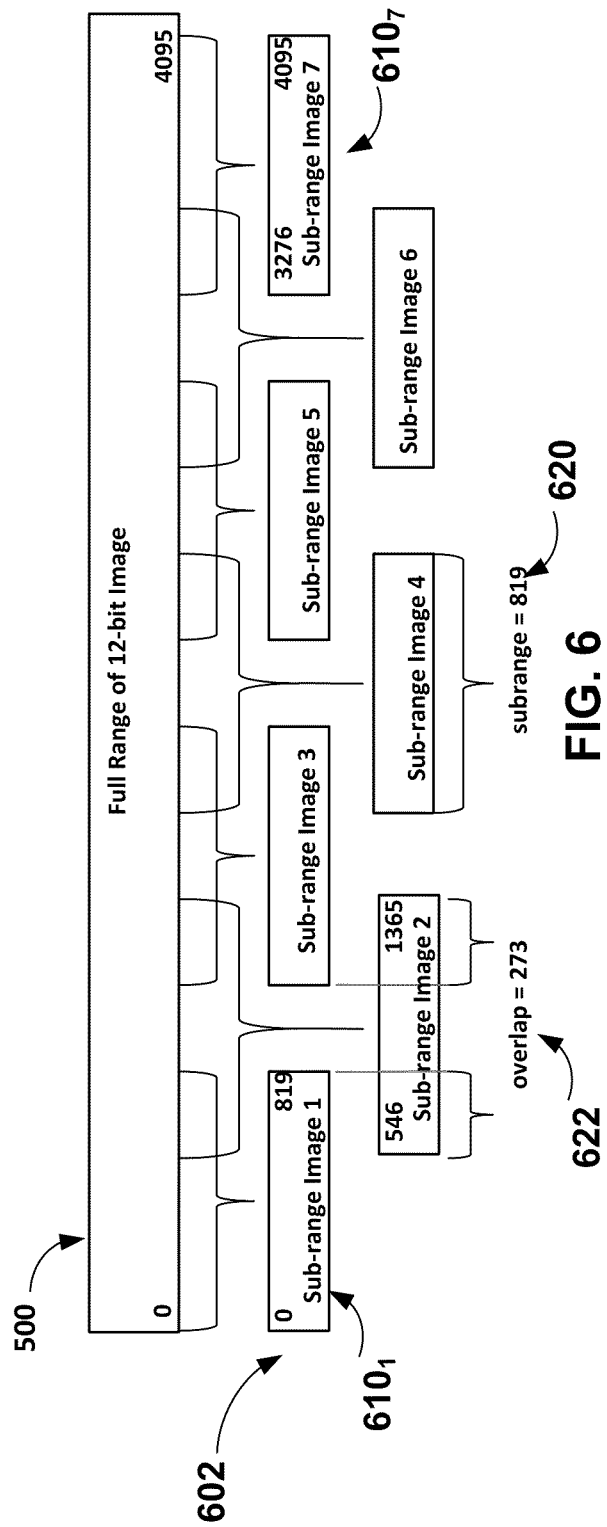
FIG. 6 is a diagram of how the sub range image, and image swapping applies to a 12 bit image according to an embodiment herein.

FIG. 6 depicts how sub-range mapping applies to a 12-bit image according to one aspect of the invention. The operation of embodiments herein do not rely on precise pixel levels, and values for thresholds, sub-ranges, sub-range overlap are included only as an example. This embodiment uses "Packed" RGB/RGBA to represent the image. In order to maximize the number of grays that can be represented by one sub-range image, additional continuous tones are packed into the available 8 bit RGB/RGBA channels (e.g., 3 channels for RGB or 4 channels if RGBA is supported). This enables an effective 8-bit pixel range that is 3 or 4 times the range that a standard color display can represent. This packing technique is important for maximum utilization of the grays available on standard computer video graphic hardware and displays. In another embodiment, the image can be represented with regular RGB values and fewer shades of gray can be displayed.

There are several ways of acquiring an image having a relatively higher bit depth including, but not limited to, leveraging 8-bit RGB/RGBA for packing more than 256 shades of gray into the pixels. RGB (766 shades) or RGBA (1021 shades), using 8-bit RGB grays: 0,0,0; 1,1,1; 2,2,2; . . . ; 255,255,255 yields 256 pixel values that when visualized result in shades of gray, using Packed RGB: 0,0,0; 0,0,1; 0,1,1; 1,1,1; 1,1,2; 1,2,2; 2,2,2; . . . ; 255,255,255 which yields 766 pixel values. When visualizing, the resulting values are first passed through a grayscale filter to map back to R=G=B values, using Packed RGBA: taking advantage of the alpha channel, to yield, in some embodiments, 1021 pixel values but otherwise similar to Packed RGB.

Here a 12-bit image 500 is displayed using a set 602 of seven sub-range images $610_1$-$610_7$ having a sub-range width 620 of 819 out of the full range of 4096. The overlap 622 between adjacent sub-range images 610 in this example is 273. Although, as shown here the overlaps 622 and sub-range widths 620 are approximately equally divided across the full range, it will be appreciated that this is not required as long as there are overlaps that satisfy the maximum achievable width for a given set.

Figure 7:
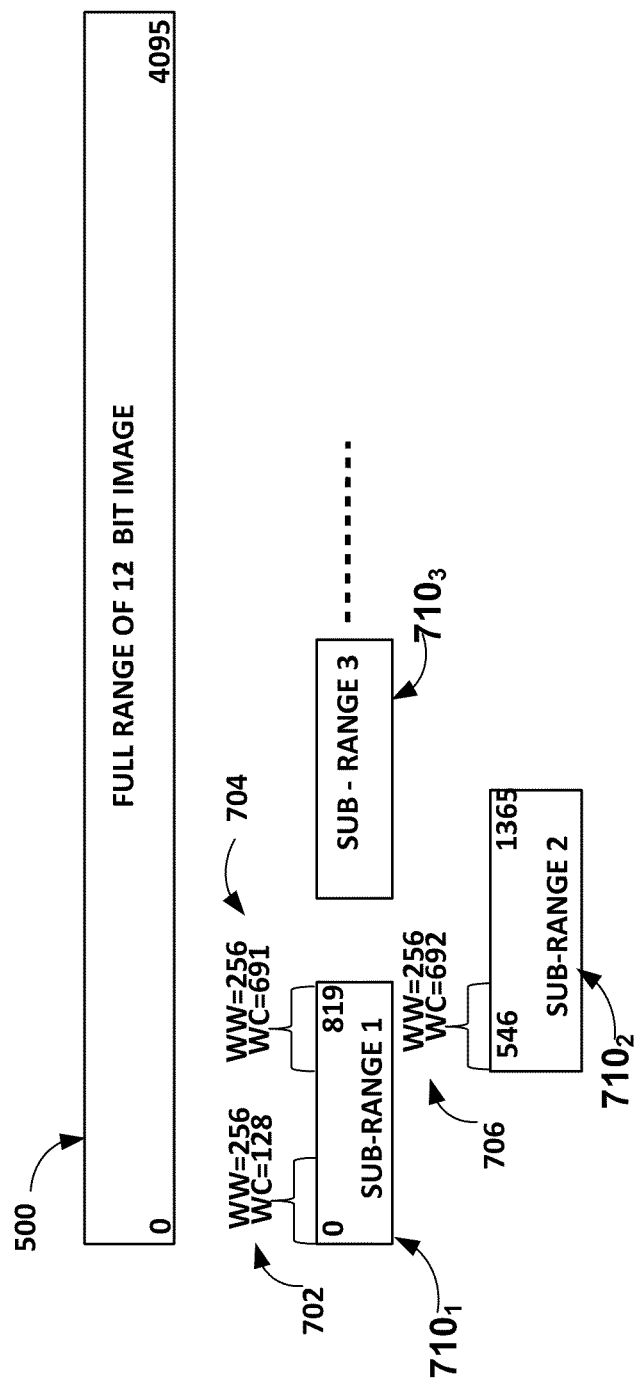
FIG. 7 is a diagram a window width and window center calculation on a 12 bit image according to an embodiment herein.

Referring now to FIG. 7, further examples of sub-range images 710 are shown. In one embodiment, simple linear calculations known in medical imaging are performed on these sub-ranges. The calculations are commonly referred to as "Windowing" an image. There are two inputs to the calculation, the window width (WW) and the window center (WC). These values can be used to define a simple linear equation that is performed on each pixel of the image. This equation can be expressed as follows:

$$y = mx + b, \text{ where:} \quad (1)$$

y is the output pixel value and x is the input pixel value
m is the range divided by WW
b is half the range minus, WC multiplied by m
or in other words $$\text{outPixelValue} = ((\text{range}/WW) * \text{inPixelValue}) + (\text{range}/2) - (WC * (\text{range}/WW)). \quad (2)$$

In other embodiments, non-linear calculations can also be performed using a lower bit-depth rendering engine.

Referring again to FIG. 7, Window calculations are performed on a source image 700 including 12-bits per pixel. The first calculation 702 shows how a window width of 256 and center of 128 is performed on the first sub-range image. When calculated for visualization, available optimized RGB image calculations are advantageously used on the sub-range image. This sub-range image is used to interactively visualize Window calculations that can be satisfied with the corresponding sub-range of pixel values.

Calculations 704 and 706 depict the behavior of the invention when a calculation crosses the boundary of the currently displayed sub-range image. The window width will stay constant for this example. In calculation 704, the window center is 691, which is the largest center value (for window width 256) that can be calculated using sub-range image 1. For this calculation sub-range image 1 $710_1$ is used for rendering. In calculation 706, the window center is 692, which is no longer able to be computed using sub-range image 1 $710_1$. For this calculation sub-range image 2 $710_2$ replaces sub-range image 1 $710_1$ for rendering and the calculations proceed accordingly.

Figure 8:
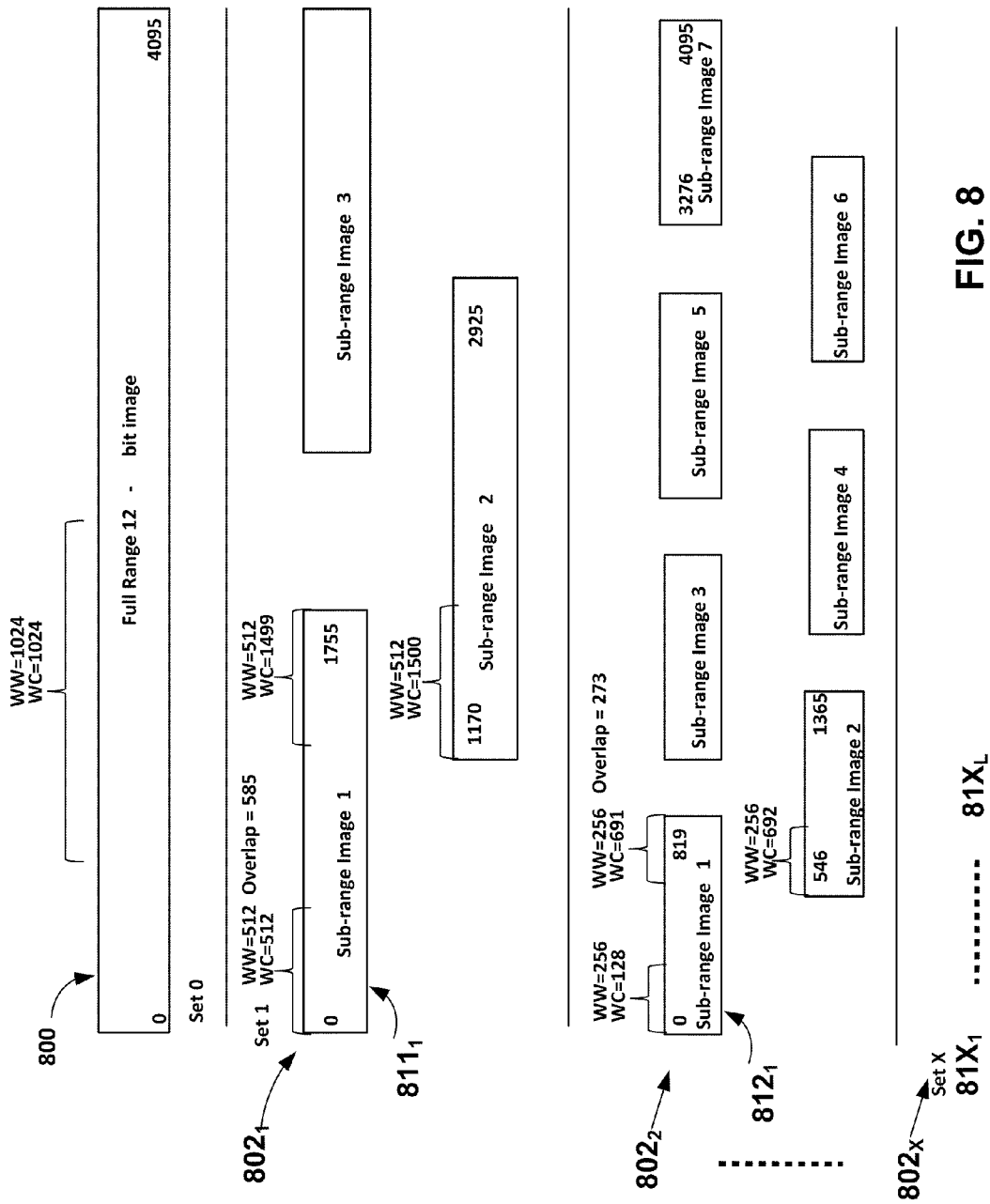
FIG. 8 is a diagram of sub-range images built for calculating window width and window center calculations on a 12 bit image according to an embodiment herein.

Referring now to FIG. 8, an application of the invention is shown for Window calculations of a source image 800 with 12 bits per pixel. Here sub-range images $811_1$-$811_3$, $812_1$-$812_7$ to $81X_1$-$81X_L$ are grouped into sub-range image sets $802_1$ to $802_X$ (generally referred to as sub-range image set 802). Each sub-range image set 802 satisfies calculations for a range of window widths. The pixel value overlap defines the maximum effective range within a set of sub-range images. The number of sub-range image set 802 and therefore the thresholds for switching between them are adjustable and can be predetermined using various criteria both objective and subjective including desired minimum grayscale values utilized at output, number of sub-range images per set desired, and total number of sets desired. Embodiments of the invention can satisfy a number of sub-range image sets 802 and any amount of overlap. Although the figures and diagrams herein suggest that the sub-range images and overlaps be fractions of the dynamic range, they can be chosen arbitrarily. The choice of these sub-range images should be made in light of the underlying optimized calculations as well as how they impact the number of images that must be generated in practical use. At the time of the per pixel calculations, the sub-range and overlap for a sub-range image set 802 are predetermined based on previously described variables and the sub-range images are generated no later than the point in time the resulting calculations are visualized. It is understood, that it is possible to determine new values for these variables and reprocess the images. In that case new sub-range images would be generated.

In operation, as a user adjusts the window width selection, the processing transitions through a window to determine which set, and the level determines which image in a sub-range image set 802. The sets $802_1$-$802_M$ and their related thresholds are defined arbitrarily in one embodiment to provide the desired grayscale quality. The image processing can be applied to any image bit depth greater than 8 bits per pixel. The more bits per pixel, the more sub-range images are necessary to provide accurate grayscale representations. For example, if the window width calculation is between 4096 and 4096/7 (approximately=585) then the full range image as input is used, this is referred to as Set 0. If the window width is between 585 and 4096/15 (approximately=273) then one of three sub-range images $811_1$ to $811_3$ is used, this set of images is referred to as Set 1. If the window width is between 273 and 1 then one of seven sub-range images $812_1$-$812_7$ is used, this set of images is referred to as Set 2. As the window width calculation changes, various sub-range images in corresponding sub-range image set are interactively displayed.

In order to use the full capability of the hardware, in one embodiment the sub-image range is set to approximately one-half of the prior set's sub image range. For example, in one embodiment to achieve a minimum of 200 levels of gray, the sub-image range is set to 200/255 of the prior set's sub-image range.

One exemplary way to determine the number of levels and their thresholds is to set a minimum number of grays that are output for a given range. For example, using packed RGB at set 0 of a 12-bit image, if the window width is reduced down to 1024, the number of grays visualized is 191 (range (4096)/window width (1024)*available grays (766)).

To ensure that that there are least 191 grays on the output side, a new sub-range image set that triggers when a window width less than 1024 is defined. In order to achieve for example a window width of 1023, sub-range images from set 1 are swapped in. Due to the costs associated with generating and storing the sub-range images in memory, the number of sub-range image sets represents a quality performance tradeoff.

Functionality associated with display embodiments will now be discussed via flowcharts in FIG. 9 through FIG. 11. For purposes of the following discussion, the rectangular elements in flowcharts, for example 910 (in FIG. 9) denote "processing blocks" and diamond shaped element, for example 1122 (in FIG. 11) denotes a decision block, and both represent computer software instructions or groups of instructions upon a computer readable medium. Additionally, the processing blocks represent steps performed by hardware such as a computer, digital signal processor circuit, application specific integrated circuit (ASIC), etc.

Figure 9:
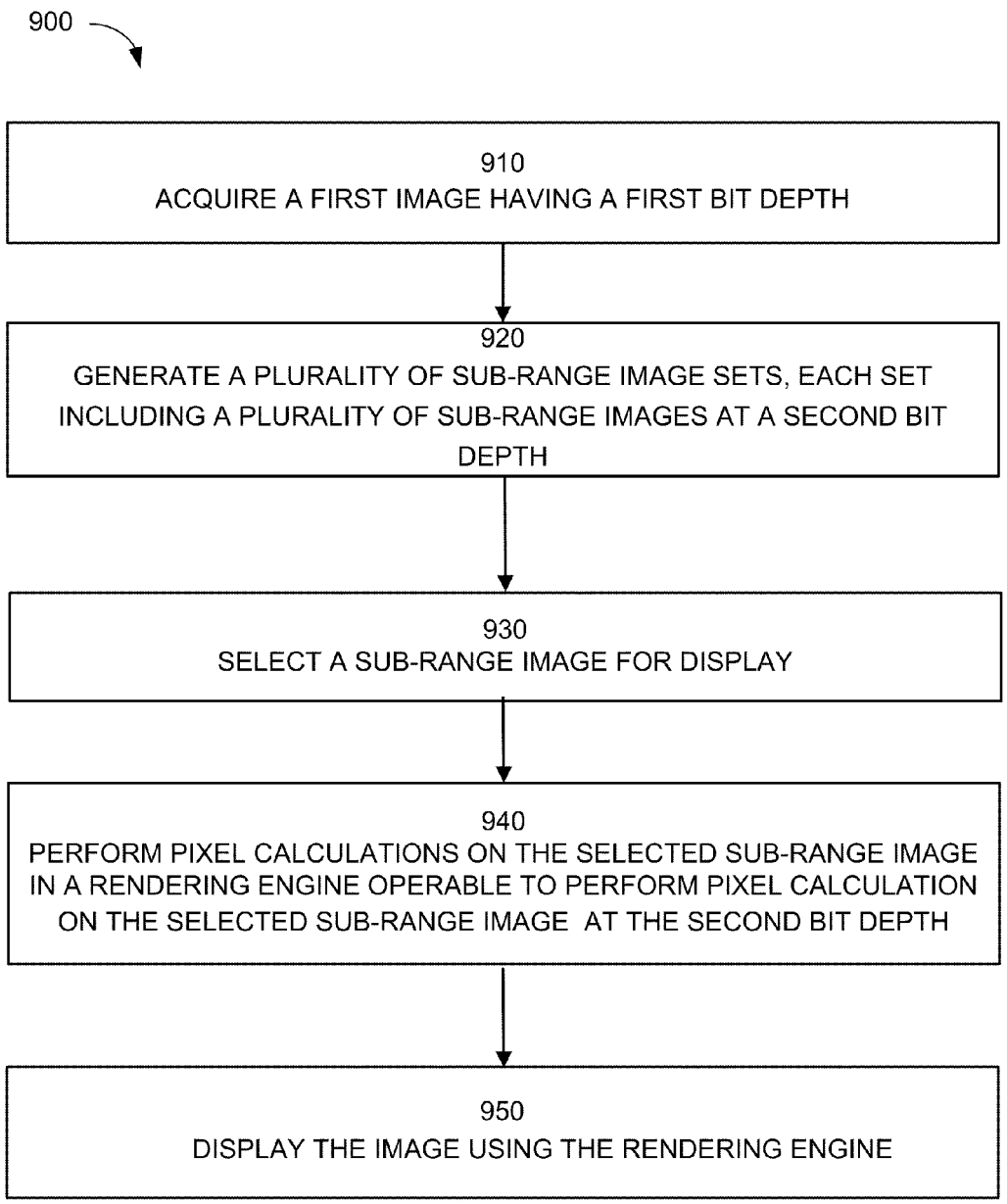
FIGS. 9-11 are flowcharts illustrating techniques associated with the viewer application according to an embodiment herein.

More particularly, FIG. 9 illustrates operations associated with an improved display of images according to embodiments herein. Note that flowchart 900 of FIG. 9 and corresponding text below may overlap with, refer to, and expand on some of the matter previously discussed with respect to FIGS. 2-8. Also, note that the steps in the flowcharts below need not always be executed in the order shown. The basic flow begins in step 910 by acquiring a first image having a first bit. After loading the full depth image, a plurality of sub-range image sets, each set including a plurality of sub-range images at a second bit depth are generated in step 920. In some embodiments, each set spans the full range of the first image, each set has a differing number of sub-range images; and each sub-range image in a set overlaps with a sub-range image in the same set. In step 930 a sub-range image is selected for display.

In step 940 pixel calculations are performed on the selected sub-range image in a rendering engine operable to perform pixel calculation on the selected sub-range image at the second bit depth. The per pixel calculations are applied to that source image, creating, in one example, a resulting 8-bit RGB/RGBA image. Finally in step 950, the image is displayed to the user using the rendering engine as shown in FIGS. 2, 3A and 3B. Further details are provided in conjunction with FIGS. 10 and 11 below.

Figure 10:
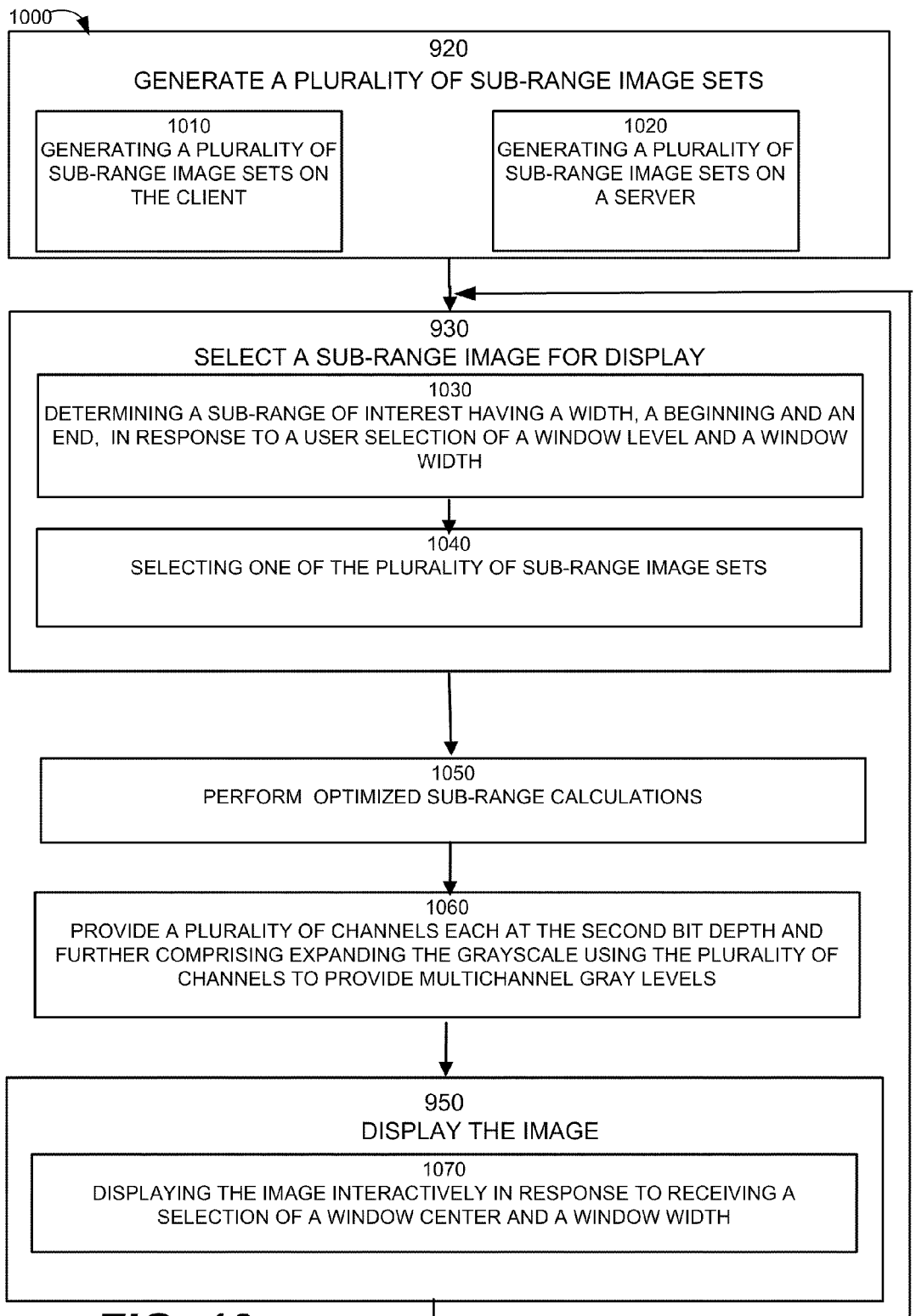

FIG. 10 is a flowchart 1000 illustrating techniques associated with the viewer application. This flowchart introduces portions of the invention as they apply to displaying calculations on a subset of the original source image bit depth. After loading the source image, appropriate sub-range images are generated in step 920. The sub-range images are generated optionally in step 1010 on the client (e.g., a PC running a web browser and providing the user display) or optionally in step 1020 on a server which serves as the image repository. While the server offloads the processing load from the client, the bandwidth requirement for transmitting the images are increased which can be problematic in limited bandwidth environments. In either step 1010 or step 1020, the sub-range images can be generated on demand or generated ahead of time after loading the full range image for display.

In step 1030, a sub-range of interest (SROI) having a width, a beginning and an end is determined in response to a user selection of a window level and a window width. Another way of determining the SROI is in response to the user selecting of one of a plurality of preset window center and window width values corresponding to the window center and the window width. In step 1040, one of the plurality of sub-range image sets is selected. In step 1050, sub-range calculations are performed. By using specialized rendering engines these calculations are optimized on a particular processor. The calculations are applied to the sub-range image to achieve the appropriate visualization. The rendering engine can operate within a client web browser or interfaced to a stand alone application.

As described above in conjunction with FIG. 6, in step 1060, the rendering engine provides a plurality of channels each at the second bit depth and the grayscale is expanded by using the plurality of channels to provide multichannel gray levels. In one embodiment, the multichannel gray scale is optionally filtered to provide true gray scale. In another embodiment, the second bit depth is 8-bits (i.e., the bit depth of the rendering engine) and the plurality of channels is either RGB or RGBA.

In step 1070, the image is interactively displayed by returning to step 930 to obtain an updated SROI in response to receiving further selections of a window center and a window width. In one embodiment, after receiving window and level adjustments, a full-depth interactive visualization is provided, in at least 256 shades of gray, of the original image, having a greater than 8-bit range, the sub-range images are transmitted over a network in an environment functionally limited by the network bandwidth connection having a rate less than 1 megabits per second and a visualization of the image is achieved in a web browser by displaying the processed sub-range image at approximately at least 15 frames per second. In another embodiment, the environment is functionally limited by the bit depth of the rendering engine and wherein the rendering engine is an 8-bit rendering engine.

Figure 11:
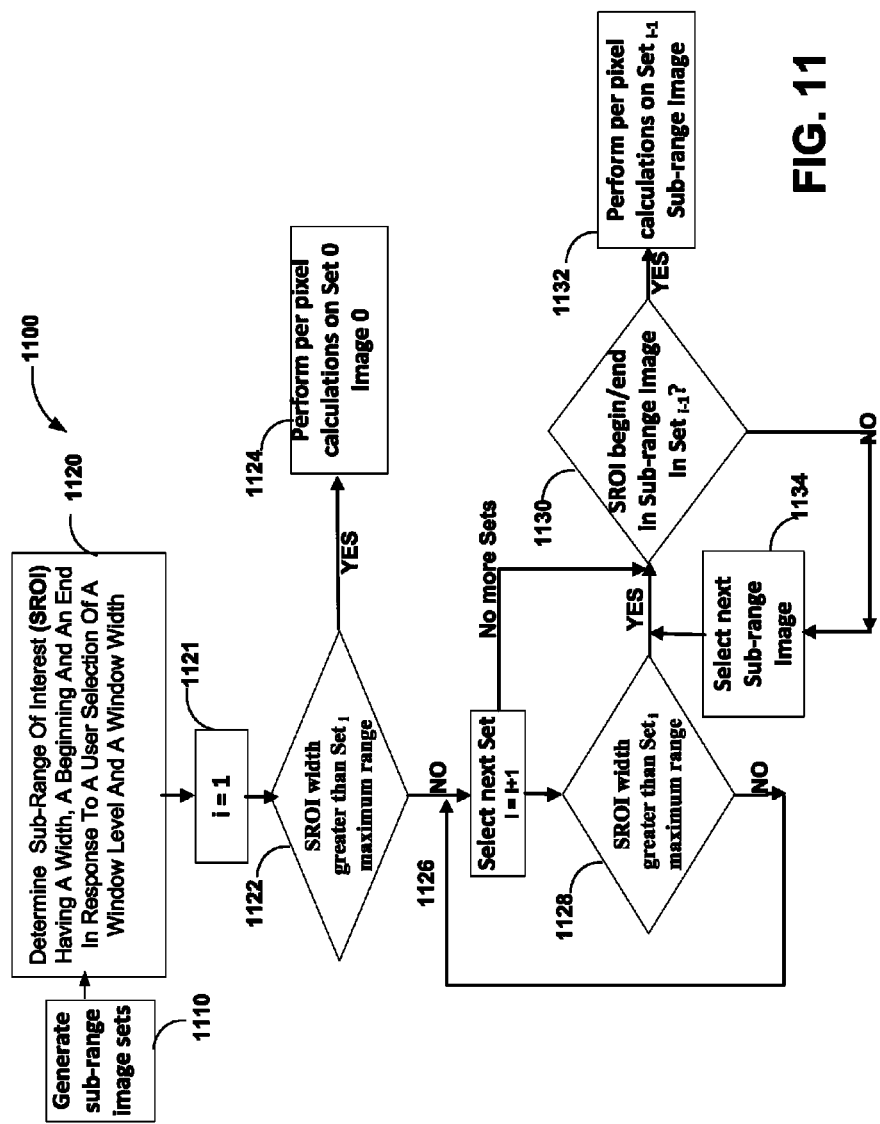

FIG. 11 is a flowchart 1100 illustrating techniques associated with the viewer application according to an embodiment herein. This flowchart describes the determination of the sub-range image that is to be used for calculations and display. The specific number of sub-range image sets and range of sub-range images within those sets are variable. In step 1110, sub-range image sets are generated. In step 1120 a sub-range of interest having a width, a beginning and an end is determined, in response to a user selection of a window level and a window width. In step 1121, the first set to be checked is set to Set 1. In step 1122, the SROI width is compared to the Set 1 maximum range. If it is determined that the SROI width is greater that Set 1 maximum range then Set 0 is selected.

Each set supports a maximum range which is used for determining which of the available sets should be used to display a selected SROI. The effective minimum range supported by a set is defined by the maximum range of the next set. The set maximum range is further determined by the overlap in that set. When trying to achieve a SROI width for display, the set and sub-range image are selected based on whether the sub-range of interest falls within the set and sub-range image (i.e. it is within the start/end ranges of the SROI.). For example referring to FIG. 8, the maximum range of Set 1 is 585 and the maximum range of Set 2 is 273. The maximum range is equal to the overlap because the overlaps are used to ensure smooth transitions between sub-range images as the SROI is interactively changed.

Step 1122 is a special case because there is only one image (the full image in the set). If it is determined that the SROI width is in Set 0, processing continues in step 1124 where per pixel calculations are performed on set 0 image 0, otherwise the process continues at step 1126.

Steps 1126 and 1128 select one of the plurality of sub-range image sets corresponding to the sub-range of interest falling within a selected set. In step 1126, the next set is selected. In step 1128, it is the SROI width is greater that Set i maximum range. If it is determined SROI width is greater that Set i (in other words that the SROI width is in the previous set), processing continues in step 1130, otherwise the process continues at step 1126 to select another set. If in step 1126, there are no more sets, then the last set is used and processing continues at step 1130.

Steps 1130 and 1134 select one of the pluralities of sub-range images in the selected set corresponding to the sub-range of interest beginning falling within the selected sub-range image for display or the sub-range end of interest falling within the selected sub-range image for display. In step 1130, it is determined if the SROI begins or ends in the selected sub-range image of the selected set of sub-range images. If it is determined that the SROI begins or ends in the selected sub-range image of the selected set of sub-range images, processing continues in step 1132 where per pixel calculations are performed on the selected sub-range image in the selected set of sub-range images, otherwise the process continues at step 1134 to select the next sub-range image and processing returns to step 1130. Referring again to FIG. 8, if for example, the SROI width is 271 and the SROI begins at 549 and ends at 820 then Set 2 is selected and sub-range image 2 $812_2$ is used for display.

For per pixel image calculations that potentially operate on a subset of the available pixel values, these techniques are applied to determine which sub-range image is used for further calculations. In one embodiment, N Sets and M sub-range images per Set are selected, the "width" or delta between the lowest and highest pixel value on which to operate are then determined. Next the Set of sub-range images to be used is determined. Each Set of sub-range images satisfies a range of width calculations. Set 0 supports the full range down to the maximum width supported by Set 1 plus 1. Set 1 supports its maximum width down to the maximum width supported by Set 2 plus 1. This continues to the last Set N.

Once the proper Set of sub-range images is determined it is determined which proper sub-range image to select for calculation and display. This is determined by the first and last values that are required by the calculation. Each sub-range image represents a subset of the original source image range. A sub-range image is then selected for which the first and last values are within said image. Depending on the sub-range and overlap variables chosen, it is possible that two images satisfy the calculation. In this case the selection of the image is arbitrary. Once the appropriate sub-range image has been identified it is used for calculations and display. The actual calculations applied to the sub-range image are derived from the mapping from the original pixel values to the sub-range images values. It is understood that there are other methods to select a sub-range image for the plurality of set as are known in the art.

Embodiments of the present invention advantageously use optimized per-pixel 8-bit RGB (or RGBA) operations in commercial off the shelf rendering engines. In one embodiment, the system uses Adobe® Flash® Player software for displaying images, and is thus available on a significantly high percentage of all personal computers which access the internet. In effect, it permits the invention to be used with no display software download. Alternatively, other rendering engines having sufficiently optimized per-pixel 8-bit RGB (or RGBA) operations can be used.

In one embodiment, Adobe's Flash® version 8 or later is used as the rendering engine. The embodiment on enables software designed to display and manipulate grayscale images in 8 bits of depth (such as Adobe® Flash® Player's filters) to display and manipulate images in greater than 8 bits of depth. In one embodiment, Flash® ActionScript code is used to perform the interactive calculations on subsets of pixel values from a continuous-tone grayscale source image having more than 8-bits per pixel. In particular, optimized 8-bit per-pixel operations, for example, the Adobe® Flash® Player flash.filters.ColorMatrixFilter are used. In this embodiment, a standard DICOM linear VOI operation specified by window width and window center values. Given other optimized 8-bit per pixel operations (such as Adobe® Flash® Player version 10's Pixel Bender interface) embodiments such as DICOM VOI LUT (Look Up Table) or DICOM VOI Function (e.g. LINEAR or SIGMOID) can be achieved. Additional detail can be found in the Digital Imaging and Communications in Medicine (DICOM) Specification, Part 3: Information Object Definitions, pages 794-796. It is understood that these techniques extend to any optimized 8-bit calculation that operates on a subset of the full range.

Figure 12:
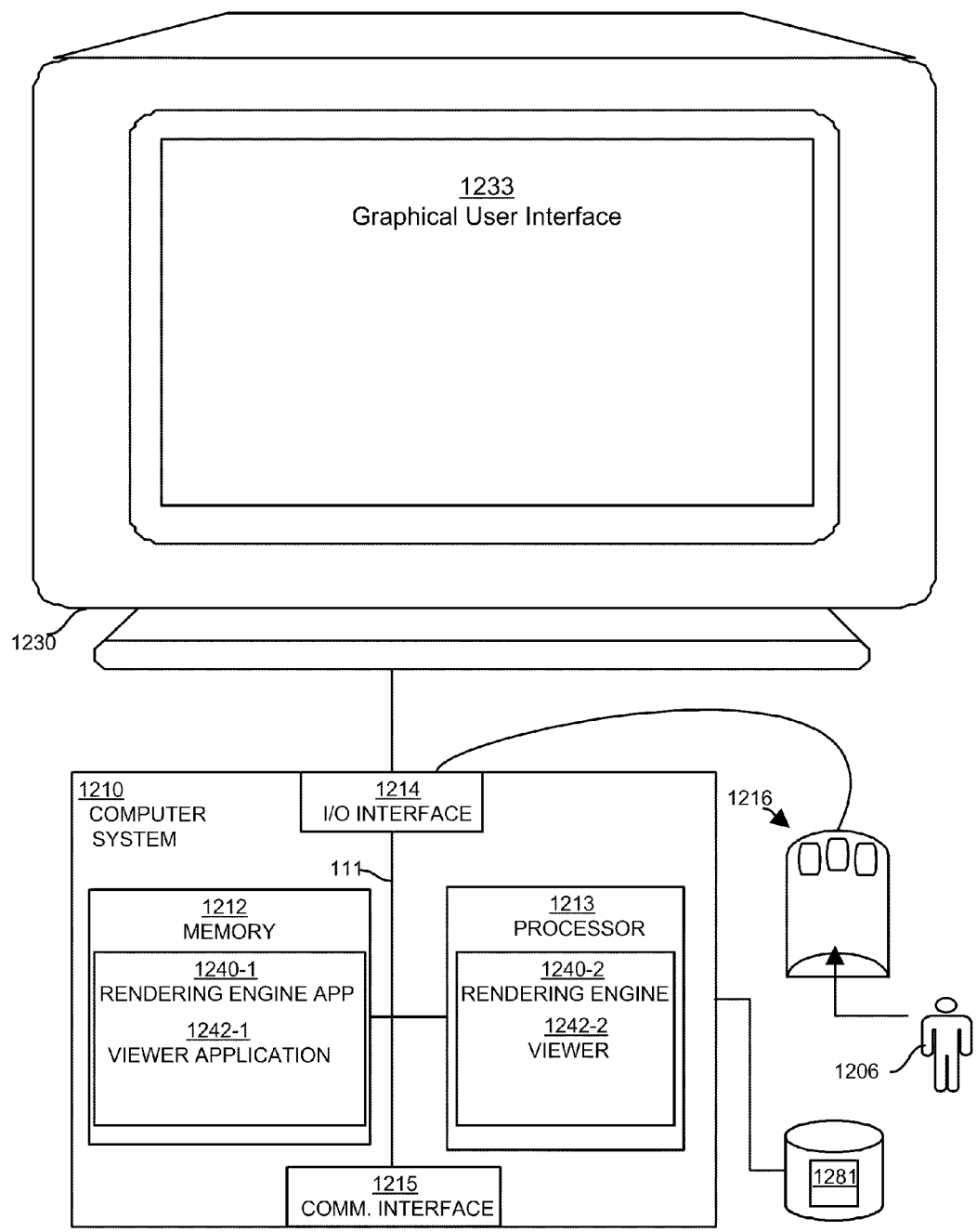
FIG. 12 is a block diagram illustrating an exemplary architecture of a computer system in a computer/network environment according to embodiments herein.

FIG. 12 is an example block diagram illustrating an architecture of a computer system 1210 that executes, runs, interprets, operates or otherwise performs a viewer process 1242-2 (e.g. an executing version of a image viewer application 1242-1 as controlled or configured by user 1206) according to embodiments herein. Note that the computer system 1210 may be any type of computerized device such as a personal computer, a client computer system, workstation, portable computing device, console, laptop, network terminal, cell phone, PDA, etc. This list is not exhaustive and is provided as an example of different possible embodiments. In addition to a single computer embodiment, computer system 1210 can include any number of computer systems in a network environment to carry the embodiments as described herein. Thus, those skilled in the art will understand that the computer system 1210 can include other processes and/or software and hardware components, such as an operating system that controls allocation and use of hardware resources, or multiple processors.

As shown in the present example, the computer system 1210 includes an interconnection mechanism 1211 such as a data bus, motherboard or other circuitry that couples a memory system 1212, a processor 1213, an input/output interface 1214, and a display 1230. Repository 1281 can optionally be used for storing documents and content both before and after processing. If so configured, the display can be used to present a graphical user interface of the viewer 1242-2 to user 1206. An input device 1216 (e.g., one or more user/developer controlled devices such as a keyboard, mouse, touch pad, touch sensitive screen, devices without keypads, speech input etc.) couples to the computer system 1210 and processor 1213 through an input/output (I/O) interface 1214. The computer system 1210 can be a client system and/or a server system. As mentioned above, depending on the embodiment, the viewer application 1242-1 and/or the viewer 1242-2 can be distributed and executed in multiple nodes in a computer network environment or performed locally on a single computer.

During operation of the computer system 1210, the processor 1213 accesses the memory system 1212 via the interconnect 1211 in order to launch, run, execute, interpret or otherwise perform the logic instructions of the viewer 1242-2. Execution of the viewer application 1242-1 in this manner produces the viewer process 1242-2. In other words, the viewer process 1242-2 represents one or more portions or runtime instances of the viewer application 1242-1 (or the entire viewer application 1242-1) performing or executing within or upon the processor 1213 in the computerized device 1210 at runtime.

The viewer application 1242-1 may be stored on a computer readable medium (such as a floppy disk), hard disk, electronic, magnetic, optical, or other computer readable medium. It is understood that embodiments and techniques discussed herein are well suited for other applications as well. Those skilled in the art will understand that the computer system 1210 may include other processes and/or software and hardware components, such as an operating system. Display 1230 need not be coupled directly to computer system 1210. For example, the viewer application 1242-1 can be executed on a remotely accessible computerized device via the communication interface 1215. The display 1230 presents a rendered graphical user interface 1260 that provides a display of content regions. The viewer 1242-2 presents a display of content regions in response to navigation commands.

Note that the following discussion provides a basic embodiment indicating how to carry out functionality associated with the viewer 1242-2 as discussed above and below. However, it should be noted that the actual configuration for carrying out the viewer 1242-2 can vary depending on a respective application. Functionality supported by computer system 1210 and, more particularly, functionality associated with viewer 1242-2 is discussed via flowcharts in FIG. 9 through FIG. 11.

While this invention has been particularly shown and described with references to preferred embodiments thereof, it will be understood by those skilled in the art that various changes in form and details may be made therein without departing from the spirit and scope of the present application as defined by the appended claims. Such variations are intended to be covered by the scope of this present application. As such, the foregoing description of embodiments of the present application is not intended to be limiting. Rather, any limitations to the invention are presented in the following claims.

What is claimed is:

1. A method for displaying an image comprising:
acquiring a first image having a first bit depth;
generating a plurality of sub-range image sets from the first image, each set including a plurality of sub-range images at a second bit depth lower than the first bit depth;
using a sub-range of interest (SROI) and a predetermined overlap parameter to determine a sub-range of at least one sub-range image in the plurality of sub-range image sets;
setting a sub-range of one of the plurality of sub-range image sets to a smaller range than a range of a different one of the plurality of sub-range image sets;
selecting a sub-range image for display;

performing pixel calculations on the selected sub-range image in a rendering engine operable to perform pixel calculation on the selected sub-range image at the second bit depth;

wherein each sub-range image in a set overlaps with a different sub-range image in the same set;

wherein the plurality of image sets spans the full range of the first image;

each set has a differing number of sub-range images;

wherein the sub-range images in each set overlap in pixel values for allowing transition between sub-range images during visualizations; and displaying the image using the rendering engine.

2. The method of claim 1, wherein selecting a sub-range image for display includes:

determining a sub-range of interest having a width, a beginning and an end, in response to a user selection of a window level and a window width; and selecting one of the plurality of sub-range image sets corresponding to the sub-range of interest falling within endpoints of the selected set.

3. The method of claim 2 further comprising selecting the sub-range image for display from one of the plurality of sub-range images in the selected set corresponding to one of:

the sub-range of interest beginning falling within the selected sub-range image for display; and the sub-range of interest end falling within the selected sub-range image for display.

4. The method of claim 1 further comprising:

receiving window and level adjustments; and providing a full-depth interactive visualization, in at least 256 shades of gray, of the first image, having a bit depth greater than an 8-bit depth;

displaying the visualization in a web browser at approximately at least 15 frames per second in an environment functionally limited by the bit depth of the rendering engine and wherein the rendering engine is an 8-bit rendering engine.

5. The method of claim 1 further comprising receiving window and level adjustments; and providing a full-depth interactive visualization, in at least 256 shades of gray, of the first image, having a bit depth greater than an 8-bit range;

transmitting the sub-range images over a network in an environment functionally limited by the network bandwidth connection having a rate less than one megabit per second; and displaying the visualization in a web browser at approximately at least 15 frames per second.

6. The method of claim 1, wherein the rendering engine is a rendering engine operable within a client web browser.

7. The method of claim 6 wherein generating a plurality of sub-range image sets at a second bit depth includes generating the plurality of sub-range image sets on the client.

8. The method of claim 6 wherein generating a plurality of sub-range image sets at a second bit depth includes generating a plurality of sub-range image sets on a server.

9. The method of claim 6 wherein the rendering engine provides a plurality of channels each at the second bit depth and further comprising:

packing shades of gray from selected overlapping sub-range images at the second bit depth from the plurality of sets, into pixels of the plurality of channels of the rendering image operating within the client web browser; and expanding the grayscale using the plurality of channels to provide multichannel gray levels.

10. The method of claim 9 further comprising visualizing the image by filtering the multichannel expanded grayscale to provide true grayscale without color components.

11. The method of claim 9 wherein the second bit depth is 8-bits and the plurality of channels are one of:

RGB; and

RGBA.

12. The method of claim 1, wherein displaying the image includes displaying the image interactively in response to receiving a selection of a window center and a window width.

13. The method of claim 12 further comprising identifying the selection of the window center and a window width based on monitoring movement of a pointer device having an indicator in a viewing region of a display screen.

14. The method of claim 12 further comprising identifying the selection of the window center and a window width based on receiving a selection of one of a plurality of preset window center and window width values.

15. The method of claim 1 further comprising determining the number of sets and range of sub-range images based on a full dynamic range and a characteristic of the first image.

16. The method of claim 15, wherein the first image is a DICOM medical image.

17. The method of claim 16, wherein the characteristic of the first DICOM image is at least one of:

a CR specific modality;

a computed tomography (CT) specific modality;

a magnetic resonance (MR) specific modality;

a mammography (MG) specific modality;

an intra-oral Radiography (IO) specific modality; and a digital radiography (DX) specific modality.

18. The method of claim 1 further comprising predetermining the SROI and the predetermined overlap parameter as a function of one of an application and an image type.

19. The method of claim 1, wherein the smaller range is approximately one-half of the range of the different one of the plurality of sub-range image sets.

20. A system for displaying an image, the system comprising:

a non-transitory computer-readable storage medium including computer program logic encoded thereon that, when executed on the system provides an image display performing operations of:

acquiring a first image having a first bit depth;

generating a plurality of sub-range image sets from the first image, each set including a plurality of sub-range images at a second bit depth lower than the first bit depth;

using a sub-range of interest (SROI) and a predetermined overlap parameter to determine a sub-range of at least one sub-range image in the plurality of sub-range image sets;

setting a sub-range of one of the plurality of sub-range image sets to a smaller range than a range of a different one of the plurality of sub-range image sets;

selecting a sub-range image for display;

performing pixel calculations on the selected sub-range image in a rendering engine operable to perform pixel calculation on the selected sub-range image at the second bit depth;

wherein each sub-range image in a set overlaps with a different sub-range image in the same set;

wherein the plurality of image sets spans the full range of the first image;

each set has a differing number of sub-range images;

wherein the sub-range images in each set overlap in pixel values for allowing transition between sub-range images during visualizations; and displaying the image using the rendering engine.

21. A computer program product having a non-transitory computer-readable storage medium including computer program logic encoded thereon that, when executed on processor within a computerized device, provides a method for displaying an image by performing the operations of:

acquiring a first image having a first bit depth;

generating a plurality of sub-range image sets from the first image, each set including a plurality of sub-range images at a second bit depth lower than the first bit depth;

using a sub-range of interest (SROI) and a predetermined overlap parameter to determine a sub-range of at least one sub-range image in the plurality of sub-range image sets;

setting a sub-range of one of the plurality of sub-range image sets to a smaller range than a range of a different one of the plurality of sub-range image sets;

selecting a sub-range image for display;

performing pixel calculations on the selected sub-range image in a rendering engine operable to perform pixel calculation on the selected sub-range image at the second bit depth;

wherein each sub-range image in a set overlaps with a different sub-range image in the same set;

wherein the plurality of image sets spans the full range of the first image;

each set has a differing number of sub-range images;

wherein the sub-range images in each set overlap in pixel values for allowing transition between sub-range images during visualizations; and displaying the image using the rendering engine.

* * * * *